United States Patent
Batz-Sohn et al.

(10) Patent No.: US 6,229,036 B1
(45) Date of Patent: *May 8, 2001

(54) SULFANYLSILANES

(75) Inventors: Christoph Batz-Sohn, Hanau; Hans-Detlef Luginsland, Köln, both of (DE)

(73) Assignee: Degussa-Hüls Aktiengesellschaft, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/407,905

(22) Filed: Sep. 29, 1999

(30) Foreign Application Priority Data

Sep. 29, 1998 (DE) .............................. 198 44 607

(51) Int. Cl.[7] ................. C07F 7/08; C07F 7/10; C08K 9/06; C08K 5/24
(52) U.S. Cl. .................. 556/426; 556/427; 556/415; 152/151; 523/209; 523/213; 523/215; 523/216; 524/155; 524/262; 524/265; 525/102; 525/342; 525/351; 525/352
(58) Field of Search ..................... 556/426, 427, 556/415; 152/151; 523/209, 213, 216; 525/102, 342, 351, 352; 524/155, 265, 262

(56) References Cited

U.S. PATENT DOCUMENTS

| 3,530,160 | * | 9/1970 | Gardner et al. | 556/427 |
| 3,654,332 | * | 4/1972 | Berger | 556/427 |
| 4,496,720 | * | 1/1985 | Bruynes et al. | 556/427 |

OTHER PUBLICATIONS

Wolf–Rüdiger Förster, "Functoinalized β–Thiolactams by Lewis Acid Catalyzed Addition of Alkynyl Silyl Sulfides to Azomethines," *Synthesis*, pp. 942–948, 1997.
Search Data, 9844607H.TRN, AKZ: 19844607, Jul. 6, 1999.

* cited by examiner

*Primary Examiner*—Paul F. Shaver
(74) *Attorney, Agent, or Firm*—Smith, Gambrell & Russell, LLP

(57) ABSTRACT

Sulfanylsilanes of the formula $X^1X^2X^3Si-A-S-SiR^1R^2R^3$ are prepared by reacting mercaptosilanes of the formula $X_1X_2X_3Si-Alkyl-SH$ with chlorosilanes $Cl-SiR_1R_2R_3$. They are used as coupling agents in rubber mixtures.

16 Claims, No Drawings

SULFANYLSILANES

INTRODUCTION AND BACKGROUND

The present invention relates to sulfanylsilanes, a process for the preparation thereof and their use.

It is known that sulfur-containing organosilicon compounds such as 3-mercaptopropyltrimethoxysilane or bis-(3-[triethoxysilyl]-propyl)tetrasulfane are used as silane coupling agents or reinforcing additives in oxidically filled rubber mixtures, inter alia for tire treads and other parts of car tires (DE 21 41 159, DE 22 12 239, U.S. Pat. No. 3,978,103, U.S. Pat. No. 4,048,206).

Furthermore, it is known that sulfur-containing silane coupling agents are used during the preparation of sealing compounds, casting moulds for metal goods, coloured and protective paints, adhesives, asphalt mixtures and oxidically filled plastics.

Other possible applications are for the fixing of active substances and functional units to inorganic support materials, for example for the immobilization of homogeneous catalysts and enzymes, for the production of fixed bed catalysts and for liquid chromatography.

The use of mercaptosilanes in rubber mixtures for tire treads is disclosed in the patent FR-A-2.094.859. Known mercaptosilanes and in particular 3-mercaptopropyltrimethoxysilane and 3-mercaptopropyltriethoxysilane are able to produce improved properties with regard to silica/elastomer coupling. The industrial use of these is not possible due to the high reactivity of the SH groups, because, during the production of the mixture, they lead to very rapid pre-vulcanization, also known as pre-scorch, with greatly increased Mooney plasticity and ultimately to mixtures which are almost impossible to process and use in an industrial situation.

For other applications such as, for example, industrial rubber items which are processed in a different way, mercaptosilanes may be used as reinforcing additives. However, in the case of almost all organic mercaptans, their intrinsic, extremely unpleasant and penetrating odor has proven to be a problem which can be only slightly reduced by mechanical means.

As a result of the pre-scorch phenomenon mentioned above, polysulfidic organosilanes, including bis-3triethoxysilyl-propyltetrasulfane or bis-3-triethoxysilylpropyldisulfane (DE 25 42 534, DE 24 05 758, DE 195 41 404, DE 197 34 295) are mostly used as coupling agents for tire treads, these seeming to be the best compromise for silica-filled vulcanizates with regard to reliability of vulcanization, simplicity of production and reinforcing power. However, these coupling reagents have to be used in relatively large amounts. Approximately 2 to 3 times as much as the amount of 3-mercaptopropyltrimethoxysilane are required to produce an equivalent level of coupling properties.

This disadvantage led to a few attempts to get round the processing difficulties by using better, in the sense of reinforcing properties, mercaptosilanes. An attempt of this kind is described in the U.S. Pat. No. 4,474,908. But this method did not produce satisfactory results with regard to scorching and processing problems and in addition is costly. Furthermore, patent EP 0 784 072 A1 describes the use of functional polyorganosiloxanes in addition to a mercaptosilane, which enabled, for the first time, the processing of mercaptosilanes as reinforcing agents in rubber mixtures for tire treads.

SUMMARY OF THE INVENTION

The invention provides sulfanylsilanes, which are characterized in that they are represented by the formula I $$X^1X^2X^3Si-A-S-SiR^1R^2R^3 \quad (I)$$

wherein $X^1$, $X^2$, $X^3$ independently, represent H, $(C_1-C_8)$alkyl, $(C_1-C_8)$alkoxy, $(C_1-C_4)$haloalkyl, aryl, $(C_7-C_{16})$aralkyl, halogen, $-A-S-SiR^1R^2R^3$ $R^1$, $R^2$, $R^3$ independently, represent H,$(C_1-C_6)$alkyl, $(C_1-C_{16})$alkoxy, $(C_1-C_{16})$haloalkyl, aryl, $(C_7-C_{16})$aralkyl, halogen, $X^1X^2X^3-A-S$ A represents a $(C_1-C_{16})$alkyl group, each of which may be linear or branched, saturated or unsaturated and may optionally be substituted with $(C_1-C_4)$alkyl, $(C_1-C_4)$alkoxy, halogen, nitrile, $(C_1-C_4)$haloalkyl, $NO_2$, $(C_1-C_4)$thioalkyl, $NR^1R^2$, $-A-S-SiR^1R^2R^3$ or $X^1X^2X^3-A-$, aryl or $(C_7-C_{16})$ aralkyl.

A preferred group of sulfanylsilanes according to the invention are characterized in that $X^1$, $X^2$, $X^3$ independently, represent $(C_1-C_4)$alkyl, $(C_1-C_4)$alkoxy, halogen $R^1$, $R^2$, $R^3$ independently, represent $(C_1-C_4)$alkyl, $(C_1-C_4)$alkoxy, halogen or $X^1X^2X^3Si-A-S$ and A represents $(C_1-C_4)$alkyl.

A further preferred groups of sulfanylsilanes according to the invention are characterized in that $X^1$, $X^2$, $X^3$ independently, represent methoxy or ethoxy, $R^1$, $R^2$, $R^3$ independently, represent methyl or $X^1X^2X^3Si-A-S$ and A represents propyl.

The expression "alkyl" is understood to cover both "straight-chain" and also "branched" alkyl groups. The expression "straight-chain alkyl group" is understood to cover, for example, groups such as methyl, ethyl, n-propyl, n-butyl, n-pentyl, n-hexyl, "branched alkyl group" is understood to cover groups such as, for example, isopropyl or tert.-butyl. The expression halogen stands for fluorine, chlorine, bromine or iodine. The expression "alkoxy" represents groups such as, for example, methoxy, ethoxy, propoxy, butoxy, isopropoxy, isobutoxy or pentoxy.

"Aryl" is understood, in the context of the invention, to cover phenyls, biphenyls or other benzenoid compounds which are optionally substituted with $(C_1-C_3)$alkyl, $(C_1-C_3)$alkoxy, halogen, hydroxyl or heteroatoms such as $NR^1R^2OR^1$, $PR^1R^2R^3$ or $SR^1$. "Aralkyl" is understood to mean that the "aryl" groups mentioned above are bonded to the corresponding silicon atom or sulfur atom or with both via a $(C_1-C_6)$alkyl chain, which for its part may be substituted with $(C_1-C_3)$alkyl, $(C_1-C_3)$alkoxy or a halogen. If the "aryl" group has a heteroatom available, such as O or S, then the $(C_1-C_6)$alkyl chain may also form a bond with the silicon atom and/or sulfur atom via the heteroatom.

In the data given for substituents, such as e.g. $(C_1-C_4)$alkoxy, the number in the subscript gives the total number of carbon atoms in the group.

Examples of sulfanylsilanes according to the invention in accordance with formula (I) are:

$(EtO)_3-Si-(CH_2)_3-S-Si(CH_3)_3$ $[(EtO)_3-Si-(CH_2)_3-S]_2Si(CH_3)_2$ $[(EtO)_3-Si-(CH_2)_3-S]_3Si(CH_3)$ $[(EtO)_3-Si-(CH_2)_3-S]_2Si(OEt)_2$ $[(EtO)_3-Si-(CH_2)_3-S]_4Si$ $(EtO)_3-Si-(CH_2)_3-S-Si(OEt)_3$ $(MeO)_3-Si-(CH_2)_3-S-Si(C_2H_5)_3$ $[(MeO)_3-Si-(CH_2)_3-S]_2Si(C_2H_5)_2$ $[(MeO)_3-Si-(CH_2)_3-S]_3Si(CH_3)$ $[(MeO)_3-Si-(CH_2)_3-S]_2Si(OMe)_2$ $[(MeO)_3-Si-(CH_2)_3-S]_4Si$ $(MeO)_3-Si-(CH_2)_3-S-Si(OMe)_3$

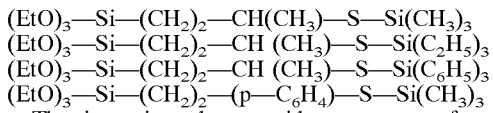
(EtO)$_3$—Si—(CH$_2$)$_2$—CH(CH$_3$)—S—Si(CH$_3$)$_3$
(EtO)$_3$—Si—(CH$_2$)$_2$—CH (CH$_3$)—S—Si(C$_2$H$_5$)$_3$
(EtO)$_3$—Si—(CH$_2$)$_2$—CH (CH$_3$)—S—Si(C$_6$H$_5$)$_3$
(EtO)$_3$—Si—(CH$_2$)$_2$—(p—C$_6$H$_4$)—S—Si(CH$_3$)$_3$ The invention also provides a process for preparing sulfanylsilanes of the general formula X$_1$X$_2$X$_3$Si—A—S—SiR$_1$R$_2$R$_3$, which is characterized in that the corresponding mercaptosilane X$_1$X$_2$X$_3$Si—Alkyl—SH is reacted with chlorosilanes Cl—SiR$_1$R$_2$R$_3$ in the presence of a base in an organic solvent, the mixture is heated to boiling point to complete the reaction, the solvent is distilled off and solid hydrochloride produced from the base is then filtered off. As an organic solvent could be used alkanes. As a base could be used triethylamine or other amines.

The corresponding sulfanylsilanes are generally so clean that possible purification by distillation is not required.

DETAILED DESCRIPTION OF INVENTION

The expression "alkyl" is understood to cover both "straight-chain" and also "branched" alkyl groups. The expression "straight-chain alkyl group" is understood to cover, for example, groups such as methyl, ethyl, n-propyl, n-butyl, n-pentyl, n-hexyl, "branched alkyl group" is understood to cover groups such as, for example, isopropyl or tert.-butyl. The expression "halogen" stands for fluorine, chlorine, bromine or iodine. The expression "alkoxy" represents groups such as, for example, methoxy, ethoxy, propoxy, butoxy, isopropoxy, isobutoxy or pentoxy.

"Aryl" is understood, in the context of the invention, to cover aromatic compounds which are substituted with (C$_1$–C$_6$)alkyl, (C$_1$–C$_6$)alkoxy, halogen or heteroatoms such as N, O, such as phenols, P- or S-substituted phenyls, biphenyls or other benzenoid compounds. "Arylalkyl" is understood to mean that the "aryl " groups mentioned above are bonded to the corresponding silicon atom via the (C$_1$–C$_6$)alkyl chain, which for its part may be substituted with (C$_1$–C$_4$)alkyl or a halogen. If the "aryl" group has a heteroatom available, such as O or S, then the (C$_1$–C$_6$)alkyl chain may also form a bond with the silicon atom via the heteroatom.

In the data given for substituents, such as e.g. (C$_1$–C$_4$) alkoxy, the number in the subscript gives the total number of carbon atoms in the group.

Surprisingly, sulfanylsilanes according to the invention are especially suitable for use in rubber mixtures.

Rubber mixtures which contain sulfanylsilanes according to the invention as coupling agents or reinforcing additives and the moulded items resulting after a vulcanization stage, in particular pneumatic tires or tire treads, have a low rolling resistance and also good wet grip and a high resistance to abrasion after performing the process according to the invention.

The present invention therefore provides rubber mixtures which contain rubber, fillers, in particular precipitated silica and optionally other rubber auxiliary substances, and at least one sulfanylsilane in accordance with the invention which is used in amounts of 0.1 to 15 wt. %, in particular 5–10 wt. %, with respect to the amount of oxidic filler used.

When using the sulfanylsilane according to the invention in rubber mixtures, there are advantages in the static and dynamic vulcanizate data produced as compared with mixtures from the prior art.

Addition of the sulfanylsilane according to the invention and addition of the filler preferably takes place at mixture temperatures of 100 to 200° C., but may also take place later at lower temperatures (40 to 100° C.), e.g. together with other rubber auxiliary agents.

The sulfanylsilane according to the invention may be added in the mixing process either in the pure form or keyed to an inert organic or inorganic support. Preferred support materials are silicas, natural or synthetic silicates, aluminum oxide or carbon black.

Suitable fillers for rubber mixtures according to the invention are:

Carbon blacks: The carbon blacks used here are prepared by the lamp black, furnace black or channel black process and have BET surface areas of 20 to 200 m$^2$/g. The carbon blacks may optionally also contain heteroatoms such as, for example, Si.

highly disperse silicas prepared, for example, by precipitation from solutions of silicates or by flame hydrolysis of silicon halides with specific surface areas of 5 to 1000, preferably 20 to 400 m$^2$/g (BET surface area) and with primary particle sizes of 10 to 400 nm. The silicas may optionally also be present as mixed oxides with other metal oxides such as Al, Mg, Ca, Ba, Zn and titanium oxides.

Synthetic silicates such as aluminum silicate, alkaline earth metal silicates such as magnesium silicate or calcium silicate, with BET surface areas of 20 to 400 m$^2$/g and primary particle diameters of 10 to 400 nm.

Natural silicates such as kaolin and other naturally occurring silicas.

Glass fibres and glass fibre products (mats, ropes) or glass micro-beads.

Carbon blacks with BET surface areas of 20 to 400 m$^2$/g or highly disperse silicas, prepared by precipitation from solutions of silicates, with BET surface areas of 20 to 400 m$^2$/g in amounts of 5 to 150 parts by wt., each with respect to 100 parts of rubber are preferably used.

The fillers mentioned may be used separately or in mixtures. In a particularly preferred embodiment of the process, 10 to 150 parts by wt. of a pale filler, optionally together with 0 to 100 parts by wt. of carbon black, and 0.1 to 15 parts by wt., preferably 5 to 10 parts by wt. of a compound of the formula (I), each with respect to 100 parts by wt. of the filler used, are used to prepare the mixtures.

Rubbers which are suitable for preparing rubber mixtures according to the invention are natural rubbers and synthetic rubbers. Synthetic rubbers are preferred, for example those described in W. Hofmann, Kautschuktechnologie, Genter Verlag, Stuttgart 1980. They include, inter alia, polybutadiene (BR)

polyisoprene (IR)

styrene/butadiene copolymers with styrene contents of 1 to 60, preferably 2 to 50 wt. % (SBR)

isobutylene/isoprene copolymers (IIR)

butadiene/acrylonitrile copolymers with acrylonitrile contents of 5 to 60, preferably 10 to 50 wt. % (NBR)

partly hydrogenated or fully hydrogenated NBR rubber (HNBR)

ethylene/propylene/diene copolymers (EPDM)

and mixtures of these rubbers. Anionic polymerised S—SBR rubbers with a glass transition temperature above −50° C. and their mixtures with diene rubbers are of particular interest for preparing vehicle tires.

Rubber vulcanizates according to the invention may also contain rubber auxiliary products such as reaction accelerators, antioxidants, heat stabilizers, light stabilizers, anti-ozonants, processing aids, plasticers, tackifiers, blowing agents, colorants, waxes, extenders, organic acids, delaying agents, metal oxides and activators such as triethanolamine, polyethylene glycol, hexanetriol, which are known within the rubber industry.

The rubber auxiliary substances are used in conventional amounts, which depend, inter alia, on the ultimate use. Conventional amounts are, for example, 0.1 to 50 wt. % with respect to the rubber. The sulfanylsilane may be used on its own as a cross-linking agent. The addition of other known cross-linking agents is generally recommended. Sulfur or peroxides may be used as other known cross-linking agents. In addition, rubber mixtures according to the invention may also contain vulcanization accelerators. Examples of suitable vulcanization accelerators are mercaptobenzthiazoles, sulfenamides, guanidines, thiurams, dithiocarbamates, thioureas and thiocarbonates. The vulcanization accelerator and sulfur or peroxide are used in amounts of 0.1 to 10 wt. %, preferably 0.1 to 5 wt. %, with respect to the rubber.

Vulcanization of rubber mixtures according to the invention may be performed at temperatures of 100 to 200° C., preferably 130 to 180° C., optionally under a pressure of 10 to 200 bar. Mixing the rubber with fillers, optionally rubber auxiliary agents and the sulfanylsilane according to the invention may be performed in conventional mixing equipment such as rollers, internal mixers and mixer-extruders. Rubber vulcanizates according to the invention are suitable for producing moulded articles, e.g. for producing pneumatic tires, tire treads, cable sleeves, hoses, drive belts, conveyor belts, roller coverings, tires, shoe soles, sealing rings and damping elements.

The disadvantages in the prior art are solved by the use of sulfanylsilanes according to the invention. Sulfanylsilanes according to the invention have very little odour. They cause the same reinforcing effect as known mercaptans. In themselves, they exhibit better processing properties than known mercaptans, such as low mixing viscosities and better scorch reliability.

EXAMPLES 1–5
Preparing Sulfanylsilanes

EXAMPLE 1

238.4 g (1.0 mol) of 3-mercaptopropyltriethoxysilane and 116.5 g (1.15 mol) of triethylamine are dissolved, one after the other, in 750 ml of petroleum ether. A solution of 108.6 g (1.0 mol) of trimethylchlorosilane in 250 ml of petroleum ether are added dropwise thereto over the course of about 1 h. The mixture is heated at boiling point for 4 h and then precipitated solids are filtered off. After removing the solvent and excess amine under vacuum, 280.5 g (0.9 mol) of 3-triethoxysilyl-propylsulfanyl-trimethylsilane are obtained in 90.3% yield as a clear, slightly yellowish liquid.
Analytical Values:
Calculated
C 46.40 H 9.34 S 10.32
Found
C 46.44 H 10.21 S 10.28

EXAMPLE 2

The same procedure is used as described in example 1, wherein 64.53 g (0.50 mol) of dichlorodimethylsilane are used instead of trimethylchlorosilane. 242.76 g (0.455 mol) of dimethyl-bis-(3-triethoxysilylpropylsulfanyl)-silane are obtained in 91.1% yield as a clear yellowish liquid.
Analytical Values:
Calculated
C 45.03 H 9.08 S 12.03
Found
C 45.35 H 9.77 S 11.77

EXAMPLE 3

The same procedure is used as described in example 1, wherein 49.83 g (0.333 mol) of trichloromethylsilane are used instead of trimethylchlorosilane. 239.48 g (0.317 mol) of methyl-tri-(3-triethoxysilylpropylsulfanyl)silane are obtained in 95.1% yield as a clear, yellowish liquid.
Analytical Values:
Calculated
C 44.52 H 8.81 S 12.73
Found
C 44.92 H 9.24 S 12.63

EXAMPLE 4

The same procedure is used as described in example 1, wherein 42.47 g (0.250 mol) of tetrachlorosilane are used instead of trimethylchlorosilane. 224.4 g (0.229 mol) of tetra-(3-triethoxysilylpropylsulfanyl)silane are obtained in 91.8% yield as a clear, yellowish liquid.
Analytical Values:
Calculated
C 44.22 H 8.66 S 13.12
Found
C 44.98 H 9.16 S 13.06

EXAMPLE 5

The same procedure is used as described in example 1, wherein 198.73 g (1.0 mol) of triethoxychlorosilane are used instead of trimethylchlorosilane. 372.63 g (0.930 mol) of 3-triethoxysilylpropylsulfanyl-triethoxysilane are obtained in 93.0% yield as a clear, yellowish liquid.
Analytical Values:
Calculated
C 44.96 H 9.06 S 8.0
Found
C 45.34 H 9.54 S 8.24

EXAMPLES 6, 7
In-rubber Tests

Examples 6 (comparison example) and 7 demonstrate the advantages of sulfanylsilanes according to the invention with regard to improved processability as compared with the mercaptosilane used in the prior art.

The general formulation used for the rubber mixtures is given in table 1 below. The unit phr means proportion by weight, with respect to 100 parts of the crude rubber used.

TABLE 1

| Substance | Amount [phr] |
| --- | --- |
| 1st stage | |
| Buna AP 341 | 100.0 |
| Ultrasil VN3 | 50.0 |
| Silane | variable |
| ZnO | 5.0 |
| Stearic acid | 1.0 |
| Renopal NS | 10.0 |
| Protector G35P | 1.0 |
| 2nd stage | |
| Batch from stage 1 | |
| Vulkacit Mercapto C | 0.75 |
| Vulkacit Thiuram C | 1.5 |
| Sulfur | 1.5 |

The polymer Buna AP 341 is an EPDM from the Hüls Co.
The silica VN3 from Degussa AG has a BET surface area of 175 m$^2$.
Renopal NS from Fuchs Mineröl-Werke GmbH Duisburg is used as a plasticiser. Vulcacit Mercapto C (MBT) and Vulkacit Thiuram C (TMTD) are commercial products from Rhein-Chemie GmbH Mannheim.

The rubber mixture is prepared in two stages in an internal mixer in accordance with the data given in table 2:

TABLE 2

| Stage 1 | |
|---|---|
| Settings | |
| Mixing unit | Werner & Pfleiderer GK 1.5E |
| Friction | 1:1 |
| Speed | 70 min-1 |
| Internal pressure | 5.5 bar |
| Empty volume | 1.58 L |
| Extent of filling | 0.55 |
| Throughput temperature | 60° C. |
| Mixing process | |
| 0 to 1 min | Buna AP 341 |
| 1 to 3 min | Ultrasil VN3, ZnO, stearic acid, Renopal NS, silane |
| 3 min | clean |
| 3 to 5 min | mix and discharge |
| Batch temperature | 140–145° C. |
| Storage | 24 h at room temperature |
| Stage 2 | |
| Settings | |
| Mixing unit | same as in stage 1 down to |
| Speed | 40 min$^{-1}$ |
| Extent of filling | 0.51 |
| Throughput temperature | 50° C. |
| Mixing process | |
| 0 to 2 min | Batch for stage 2 + Vulkacit Mercapto C + Vulkacit Thiuram C + sulfur |
| 2 min | discharge and form a sheet on a laboratory roller mixer (diameter 200 mm, length 450 mm, throughput temperature 50° C.) then extract a sheet |
| Batch temperature | 100–110° C. |

The vulcanization time for the test specimens is 60 minutes at 170° C.

The rubber engineering test is performed in accordance with the test methods given in table 3.

TABLE 3

| Physical tests | Standard/conditions |
|---|---|
| ML 1 + 4, 100° C. | DIN 53523/3, ISO 667 |
| Cure-meter test, 165° C. | DIN 53529/3, ISO 6502 |
| Tensile test on a ring, 23° C. | DIN 53504, ISO 37 |
| Tensile strength | |
| Modulus | |
| Elongation at break | |
| Shore A hardness, 23° C. | DIN 53 505 |
| Ball rebound, 0 and 60° C. | ASTM D 5308 |
| Viscoelastic properties, 0 and 60° C., 16 Hz, 50 N prelim. force and 25 N amplitude force Complex modulus E*, Loss factor tan δ | DIN 53 513, ISO 2856 |
| Goodrich flexometer, 25 min at 23° C. and 0.175 inch stroke | DIN 53 533, ASTM D 623 A |
| DIN abrasion, 10 N force | DIN 53 516 |
| Pressure forming residue DVR, 22 h at 70° C. | DIN 53 517, ISO 815 |
| Dispersion | ISO/DIS 11345 |

In comparison example 6, 2.4 parts of KBM-803, a 3-mercaptopropyltrimethoxysilane, obtainable from Shin-Etsu, are added.

In example 7, 3.8 parts of the sulfanylsilane according to example 1 are used. This corresponds to equimolar addition, with respect to the mercaptosilane in comparison example 6.

The following rubber engineering data are determined for the crude mixture and for the vulcanizate (table 4):

TABLE 4

| Crude mixture results | | | |
|---|---|---|---|
| Feature: | Units | Example 6 | Example 7 |
| MDR 150° C. | | | |
| D120-Dmin | [dNm] | 19.6 | 26.7 |
| t 10% | [min] | 1.02 | 1.90 |
| t 90% | [min] | 75.1 | 70.2 |
| Marching modulus | [%] | 16 | 13 |
| ML 1 + 4 100° C. 2nd stage | [ME] | 120 | 101 |
| Vulcanisate results | | | |
| Feature: | Units | 1 | 2 |
| Tensile test on a ring | | | |
| Tensile strength | [MPa] | 12.3 | 16.9 |
| Modulus 100% | [MPa] | 2.4 | 2.5 |
| Modulus 300% | [MPa] | 8.3 | 9.1 |
| Elongation at break | [%] | 400 | 460 |
| Fracture energy | [J] | 71.6 | 108.7 |
| Shore A hardness (23° C.) | [SH] | 70 | 73 |
| DIN abrasion | [mm$^3$] | 96 | 96 |
| DVR 22 h at 70° C. | [%] | 25.7 | 20.8 |

As shown in table 4, the sulfanylsilane according to the invention produces a lower mixing viscosity and improved scorch behaviour (t10%). In addition, for equimolar addition, higher moduli and tensile strengths are achieved and a lower pressure forming residue is found.

EXAMPLES 8–9

Examples 8 to 9 show that the use of sulfanylsilanes according to the invention leads to a higher coupling yield between silica and rubber. This is shown by the higher moduli and improved hysteresis behaviour.

The formulation used is given in table 5. Here the unit phr means the proportion by weight, with respect to 100 parts of the crude rubber used.

TABLE 5

| Substance | Amount [phr] |
|---|---|
| 1st stage | |
| Buna VSL 5025-1 | 96.0 |
| Buna CB 24 | 30.0 |
| Ultrasil VN3 | 80.0 |
| ZnO | 3.0 |
| Stearic acid | 2.0 |
| Naftolene ZD | 10.0 |
| Vulkanox 4020 | 1.5 |
| Protector G35P | 1.0 |
| TESPD | 6.4 |
| 2nd stage | |
| Batch from stage 1 | |
| 3rd stage | |
| Batch from stage 2 | |

TABLE 5-continued

| Substance | Amount [phr] |
|---|---|
| Vulkacit D | 2.0 |
| Vulkacit CZ | 1.5 |
| Sulfur | 2.1 |

The polymer VSL 5025-1 is a solution polymerized SBR copolymer from Bayer AG with a stirene content of 25 wt. % and a butadiene content of 75 wt. %. The butadiene is 73% 1,2, 10% cis 1,4 and 17% trans 1,4 linked. The copolymer contains 37.5 phr of oil and has a Mooney viscosity (ML 1+4/100° C.) of about 50.

The polymer Buna CB 24 is a cis 1,4 polybutadiene (Titan type) from Bayer AG with a cis 1,4 content of 92%, a trans 1,4 content of 4%, a 1,2 content of 4% and a Mooney viscosity between 44 and 50.

The silica VN3 from Degussa AG has a BET surface area of 175 m²/g.

Bis-(3-[triethoxysilyl]-propyl)disulfane (TESPD) is prepared in accordance with the patent DE 197 34 295 and has a disulfane content of >80%.

Naftolen ZD from Chemetall is used as an aromatic oil. Vulkanox 4020 is a PPD from Bayer AG. Protektor G35P is an anti-ozonant wax from HB-Fuller GmbH. Vulkacit D (DPG) and Vulkacit CZ (CBS) are commercial products from Bayer AG.

The rubber mixture is prepared in three stages in an internal mixer in accordance with table 6:

TABLE 6

Stage 1

| Settings | |
|---|---|
| Mixing unit | Werner & Pfleiderer GK 1.5E |
| Friction | 1:1.11 |
| Speed | 70 min-1 |
| Internal pressure | 5.5 bar |
| Empty volume | 1.6 L |
| Extent of filling | 0.55 |
| Throughput temperature | 80° C. |
| Mixing process | |
| 0 to 1 min | Buna VSL 5025-1 + Buna CB 24 |
| 1 to 3 min | ½ Ultrasil VN3, ZnO, stearic acid, Naftolen ZD, silane |
| 3 to 4 min | ½ Ultrasil VN3, Vulkanox 4020, Protector G35P |
| 4 min | clean |
| 4 to 5 min | mix |
| 5 min | clean |
| 5 to 6 min | mix and discharge |
| Batch temperature | 140–150° C. |
| Storage | 24 h at room temperature |

Stage 2

| Settings | |
|---|---|
| Mixing unit | same as in stage 1 down to: |
| Speed | 80 min⁻¹ |
| Extent of filling | 0.53 |
| Throughput temperature | 80° C. |
| Mixing process | |
| 0 to 2 min | Break up batch from stage 1 |
| 2 to 5 min | Keep batch temperature at 150° C. by varying the speed |
| 5 min | discharge |

TABLE 6-continued

| Batch temperature | 150–155° C. |
|---|---|
| Storage | 4 h at room temperature |

Stage 3

| Settings | |
|---|---|
| Mixing unit | same as in stage 1 down to |
| Speed | 40 min⁻¹ |
| Extent of filling | 0.51 |
| Throughput temperature | 50° C. |
| Mixing process | |
| 0 to 2 min | Batch from stage 2 + Vulkacit CZ + Vulkacit D + sulfur |
| 2 min | discharge and form a sheet on a laboratory mixing roller (diameter 200 mm, length 450 mm, throughput temperature 50° C.) Homogenise: 3* left, 3* right cut in and fold round and pass throuqh 8* with narrow roller gap (1 mm) and 3* with wide roller gas (3.5 mm) and finally draw out as a sheet. |
| Batch temperature | 90–100° C. |

The general procedure for preparing rubber mixtures and heir vulcanisates is described in the following book: "Rubber Technology Handbook", W. Hofmann, Hanser Verlag 1994.

The vulcanizing time for the test items was 50 minutes at 165° C.

Rubber engineering testing was performed in accordance with the test methods given in table 3.

In accordance with example 8, 8.4 parts of the organo-silicon compound (sulfanylsilane) according to the invention from example 1 were added to the mixture in example 9 instead of 6.4 parts of bis-[3-triethoxysilyl]-propyl) disilane (TESPD). This corresponds to equimolar addition with respect to the triethoxysilyl units.

The rubber engineering data determined for the crude mixture and the vulcanisate are given in table 7:

TABLE 7

Crude rubber results

| Feature: | | Example 8 | Example 9 |
|---|---|---|---|
| MDR 165° C. | | | |
| Dmax-D120 | [dNm] | 16.3 | 11.0 |
| t 10% | [min] | 2.00 | 0.49 |
| t 90% | [min] | 13.3 | 15.75 |
| Marching modulus | [%] | 2.2 | 2.1 |

Vulcanisate results

| Feature: | Units | 6 | 7 |
|---|---|---|---|
| Tensile test on a ring | | | |
| Tensile strength | [MPa] | 13.7 | 13.2 |
| Modulus 100% | [MPa] | 2.5 | 2.2 |
| Modulus 300% | [MPa] | 12.4 | 13.6 |
| Elongation at break | [%] | 320 | 290 |
| Fracture energy | [J] | 57.1 | 47.6 |
| Shore A hardness (23° C.) | [SH] | 66 | 59 |
| Ball rebound (0° C.) | [%] | 11.1 | 10.0 |

TABLE 7-continued

| | | | |
|---|---|---|---|
| Ball rebound (60° C.) | [%] | 58.4 | 65.8 |
| DIN abrasion | [mm³] | 63 | 45 |
| Viscoelastic test | | | |
| Dyn. mod. of exp. E* (0° C.) | [MPa] | 24.2 | 17.2 |
| Dyn. mod. of exp. E* (60° C.) | [MPa] | 8.3 | 7.5 |
| Loss factor tan δ (0° C.) | [—] | 0.493 | 0.473 |
| Loss factor tan δ (60° C.) | [—] | 0.119 | 0.103 |
| Dispersion | [—] | 8 | 8 |

As can be seen from table 7, the use of a sulfanylsilane according to the invention in accordance with example 1 leads to a similar modulus value and a lower abrasion value, despite the reduced hardness of the mixture. In addition, there is a clearly lower tan δ (60° C.) value, a measure of the energy loss under dynamic stress. This demonstrates the higher silica/rubber coupling yield due to the sulfanylsilane according to the invention.

Further variations and modifications of the foregoing will be apparent to those skilled in the art and are intended to be encompassed by the claims appended hereto.

German priority application 198 44 607.1 filed Sep. 29, 1998 is relied on and incorporated herein by reference.

We claim:

1. A sulfanylsilane represented by formula I $$X^1X^2X^3Si\text{—}A\text{—}S\text{—}SiR^1R^2R^3 \quad (I),$$

wherein $X^1$ represents $(C_1\text{–}C_8)$ alkoxy;

$X^2$, $X^3$ independently, represent H, $(C_1\text{–}C_8)$ alkyl, $(C_1\text{–}C_8)$ alkoxy, $(C_1\text{–}C_4)$ haloalkyl, aryl, $(C_7\text{–}C_{16})$ aralkyl, halogen, or —A—S—$SiR^1R^2R^3$;

$R^1$, $R^2$, $R^3$ independently, represent H, $(C_1\text{–}C_{16})$ alkyl, $(C_1\text{–}C_{16})$ alkoxy, $(C_1\text{–}C_{16})$ haloalkyl, aryl, $(C_7\text{–}C_{16})$ aralkyl, halogen, or $X^1X^2X^3$—A—S; and A represents a $(C_1\text{–}C_{16})$ alkyl, each of which may be linear or branched, saturated or unsaturated and optionally may be substituted with $(C_1\text{–}C_4)$ alkyl, $(C_1\text{–}C_4)$ alkoxy, halogen, nitrile, $(C_1\text{–}C_4)$ haloalkyl, $NO_2$, $(C_1\text{–}C_4)$ thioalkyl, $NR^1R^2$, —A—S—$SiR^1R^2R^3$ or $X^1X^2X^3$—A—, aryl or $(C_7\text{–}C_{16})$ aralkyl.

2. The Sulfanylsilane according to claim 1, wherein $X^1$, $X^2$, $X^3$ independently, represent $(C_1\text{–}C_4)$alkyl, $(C_1\text{–}C_4)$ alkoxy, or halogen $R^1$, $R^2$, $R^3$ independently, represent $(C_1\text{–}C_4)$alkyl, $(C_1\text{–}C_4)$alkoxy, halogen or $X^1X^2X^3Si\text{—}A\text{—}S$ and A represents $(C_1\text{–}C_4)$alkyl.

3. The sulfanylsilane according to claim 1, wherein $X^1$, $X^2$, $X^3$ independently, represent methoxy or ethoxy, $R^1$, $R^2$, $R^3$ independently, represent methyl or $X^1X^2X^3Si\text{—}A\text{—}S$ and A represents propyl.

4. A process for preparing a sulfanylsilane of the general formula $X^1X_2X_3Si\text{—}alkyl\text{—}S\text{—}SiR_1R_2R_3$ according to claim 1, comprising reacting a corresponding mercaptosilane of the formula $X^1X_2X_3Si\text{—}alkyl\text{—}SH$ with a chlorosilane of the formula $Cl\text{—}SiR_1R_2R_3$ and recovering the product.

5. The process according to claim 4 further comprising reacting in the presence of a base in an organic solvent to form a reaction mixture.

6. The process according to claim 5 further comprising heating said mixture to the boiling point of the mixture to complete the reaction.

7. The process according to claim 6 further comprising distilling off the solvent.

8. The process according to claim 7 further comprising filtering off solid hydrochloride.

9. A rubber mixture comprising rubber, an oxidic filler, and optionally a further rubber auxiliary substance and at least one sulfanylsilane according to claim 1 in an amount of 0.1 to 15 wt. %, with respect to the amount of oxidic filler used.

10. The rubber mixture according to claim 9 wherein the oxidic filler is precipitated silica.

11. A rubber tire made from the mixture according to claim 9.

12. A rubber mixture comprising rubber, an oxidic filler and the sulfanylsilane according to claim 2.

13. A rubber mixture comprising rubber, an oxidic filler and the sulfanylsilane according to claim 3.

14. A process for making an improved rubber product comprising mixing rubber, an oxidic filler and a sufficient amount of the sulfanylsilane according to claim 1, and vulcanizing the resulting mixture to form the rubber product.

15. The process according to claim 14 wherein said filler, rubber and sulfanylsilane are mixed together at a temperature of 100 to 200° C.

16. The process according to claim 14 wherein the silane and filler are added to the rubber at a temperature of 40 to 100° C.

* * * * *